(12) United States Patent
Breard et al.

(10) Patent No.: US 7,361,757 B2
(45) Date of Patent: Apr. 22, 2008

(54) METHOD FOR SYNTHESIZING ESTERS OF N-[(S)-1-CARBOXYBUTYL]-(S)-ALANINE AND USE THEREOF FOR SYNTHESIZING PERINDOPRIL

(75) Inventors: Fabienne Breard, Petit-Quevilly (FR); Claude Fugier, Gruchet le Valasse (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 267 days.

(21) Appl. No.: 10/569,472

(22) PCT Filed: Aug. 31, 2004

(86) PCT No.: PCT/FR2004/002213

§ 371 (c)(1), (2), (4) Date: Feb. 22, 2006

(87) PCT Pub. No.: WO2005/023755

PCT Pub. Date: Mar. 17, 2005

(65) Prior Publication Data

US 2006/0252958 A1    Nov. 9, 2006

(30) Foreign Application Priority Data

Sep. 1, 2003  (EP) .................. 03292145

(51) Int. Cl.
*C07D 265/32* (2006.01)

(52) U.S. Cl. .................. 544/173; 544/106; 544/170
(58) Field of Classification Search ............... 544/106, 544/170, 173
See application file for complete search history.

(56) References Cited

FOREIGN PATENT DOCUMENTS

EP        0308340        3/1989

OTHER PUBLICATIONS

International Preliminary Examination Report for PCT/FR2004/002213 of Jul. 13, 2006.
W. Baker, et al., "Synthesis of the nonpeptide rennin inhibitor A-68064 and the ACE inhibitor methyl enalaprilat from (5S)-2,3,5,6-tetrahydro-5-alkyl-N-(tertbutyloxycarbonyl)-4H-1,4-oxazine-2-ones" Tetrahedron Letters, 33(12), pp. 1577-1588, 1992.
W. Baker, et al., "Synthesis and structure determination of (3S, 5S)-2,3,5,6-tetrahydro-3,5-dialkyl-N-(tert-butyloxycarbonyl)-4H-1, 4-oxazine-2-ones" Tetrahedron Letters, 33(12), pp. 1573-1576, 1992.
International Search Report for PCT/FR2004/002213, Jan. 7, 2005.
Europen Search Report for EP 03292145, Jan. 27, 2004.

*Primary Examiner*—Golam M. M. Shameem
(74) *Attorney, Agent, or Firm*—Hueschen and Sage

(57) ABSTRACT

A process for the synthesis of compounds of formula (I):

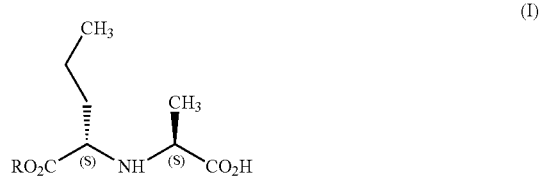

wherein R represents a linear or branched ($C_1$-$C_6$)alkyl group.

Application in the synthesis of perindopril and its pharmaceutically acceptable salts.

8 Claims, No Drawings

METHOD FOR SYNTHESIZING ESTERS OF N-[(S)-1-CARBOXYBUTYL]-(S)-ALANINE AND USE THEREOF FOR SYNTHESIZING PERINDOPRIL

The present invention relates to a process for the synthesis of N-[(S)-1-carboxybutyl]-(S)-alanine esters, and to their application in the synthesis of perindopril and its pharmaceutically acceptable salts.

More specifically, the present invention relates to a new process for the synthesis of the compounds of formula (I):

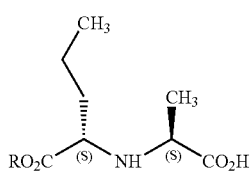

(I)

wherein R represents a linear or branched $(C_1-C_6)$alkyl group, and addition salts thereof with a mineral or organic acid or base.

The compounds of formula (I) obtained according to the process of the invention are useful in the synthesis of perindopril of formula (II):

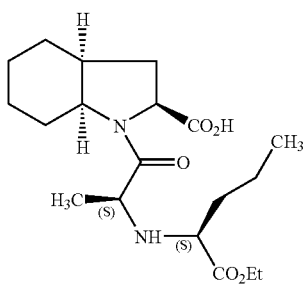

(II)

and in the synthesis of its pharmaceutically acceptable salts.

Perindopril and its pharmaceutically acceptable salts have valuable pharmacological properties.

Their principal property is that of inhibiting angiotensin I converting enzyme (or kininase II), which allows, on the one hand, prevention of the conversion of the decapeptide angiotensin I to the octapeptide angiotensin II (a vasoconstrictor) and, on the other hand, prevention of the degradation of bradykinin (a vasodilator) to an inactive peptide.

Those two actions contribute to the beneficial effects of perindopril in cardiovascular diseases, more especially arterial hypertension and heart failure.

Perindopril, its preparation and its use in therapeutics have been described in the European patent specification EP 0 049 658.

In view of the pharmaceutical value of that compound, it has been important to be able to obtain the intermediate of formula (I) by an effective synthesis process that allows in particular, the selective production of the (S,S) diastereoisomer in a good yield and with an excellent degree of purity, but that is equally readily transposable to an industrial scale.

Some methods for the preparation of the compounds of formula (I) are already known.

The journal Tet. Lett. 1982, 23 (16), 1677-80 describes the production of a compound of formula (I) (R=ethyl) by the reaction in ethanol of ethyl 2-oxovalerate with alanine tert-butyl ester in the presence of sodium cyanoborohydride.

The patent specification EP 0 309 324 describes the production of a compound of formula (I) (R=ethyl) by the reaction in dimethylformamide of alanine benzyl ester with ethyl α-bromovalerate in the presence of triethylamine.

The patent specifications EP 0 308 340 and EP 0 308 341 describe the production of a compound of formula (I) (R=ethyl) by the reaction in water of ethyl norvalinate hydrochloride with pyruvic acid in the presence of hydrogen, palladium-on-carbon and sodium hydroxide.

The Applicant has now developed a new process for the industrial synthesis of compounds of formula (I).

More specifically, the present invention relates to a process for the synthesis of compounds of formula (I) which is characterised in that a morpholinone of formula (III):

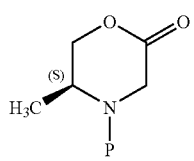

(III)

wherein P represents a protecting group for the amino function, is reacted
either with allyl bromide or allyl triflate, in the presence of a base, to yield a compound of formula (IV) having the (3S,5S) configuration:

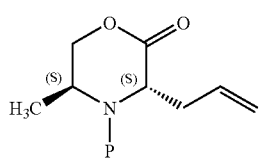

(IV)

wherein P is as defined hereinbefore,
which is hydrogenated in the presence of palladium-on-carbon,
or with iodopropane,
to yield a compound of formula (V) having the (3S,5S) configuration:

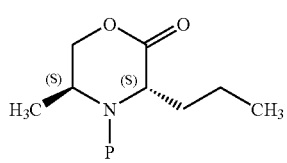

(V)

wherein P is as defined hereinbefore,
which is subjected to the action of LiOH, then to the action of an esterification reagent, to yield a compound of formula (VI):

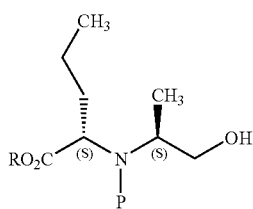

(VI)

wherein R and P are as defined hereinbefore, which is reacted with an oxidising agent to yield, after deprotection of the amino function, the compound of formula (I).

Among the protecting groups for the amino function that can be used in the present invention there may be mentioned, without implying any limitation, the groups tert-butoxycarbonyl and benzyloxycarbonyl. The preferred P group is the tert-butoxycarbonyl group.

Among the bases that can be used for the reaction between the compound of formula (III) and allyl bromide or allyl triflate there may be mentioned, without implying any limitation, lithium diisopropylamide (LDA), sodium bis(trimethylsilyl)amide (NaHMDS) and potassium tert-butanolate.

Among the esterification reagents that can be used for the formation of the compound of formula (VI) there may be mentioned, as preferred, the compounds of formula (VII):

R—X    (VII)

wherein R is as defined for formula (I), and X represents a triflate, tosylate or mesylate group or a halogen atom, preferably iodine.

When it is desired to obtain compounds of formula (I) wherein R represents a methyl group, the esterification reagent may also be diazomethane.

Among the oxidising agents that can be used for the oxidation of the compound of formula (VI) there may be mentioned, without implying any limitation, $NaIO_4$ in the presence of $RuCl_3$.

The oxidation may also be carried out in two steps, by first converting the compound of formula (VI) to the corresponding aldehyde, for example under Swern conditions, then oxidising the aldehyde to the corresponding carboxylic acid, for example using $KMnO_4$.

The compounds of formula (V) and (VI) are new products, useful as synthesis intermediates in the chemical or pharmceutical industry, especially in the synthesis of perindopril, and as such form an integral part of the present invention.

The group R that is preferred is the ethyl group.

The compound of formula (III) can be obtained starting from (S)-N-benzylalaninol, which is reacted with ethyl bromoacetate in the presence of triethylamine to yield, after cleaving the benzyl group, (S)-N-(ethoxycarbonylmethyl)alaninol, which is then protected by the group P as defined hereinbefore, which is then cyclised by reaction with para-toluenesulphonic acid.

EXAMPLE

N-[(S)-Ethoxycarbonyl-1-butyl]-(S)-alanine hydrochloride

Step A: tert-Butyl (3S,5S)-3-allyl-5-methyl-2-oxo-4-morpholinecarboxylate:

Introduce into a reactor 200 g of tert-butyl (5S)-5-methyl-2-oxo-4-morpholinecarboxylate and 700 ml of tetrahydrofuran, then cool the solution to −60° C. and add 700 ml of a 2M solution of lithium diisopropylamide in tetrahydrofuran and heptane, while maintaining the temperature of the reaction mixture below −40° C. After reaction for 1 hour, add 225 g of allyl bromide while maintaining the temperature of the reaction mixture at −30° C., and stir for 3 hours.

Subsequently, return the reaction to ambient temperature, hydrolyse with an aqueous ammonium chloride solution, extract with ether and wash the ethereal phase with water.

The tert-butyl (3S,5S)-3-allyl-5-methyl-2-oxo-4-morpholinecarboxylate isolated by concentrating the ethereal phase to dryness is used as it is in the following Step.

Step B: tert-Butyl (3S,5S)-5-methyl-3-propyl-2-oxo-4-morpholinecarboxylate:

Introduce into a hydrogenation vessel 200 g of the compound obtained in the above Step in solution in ethanol, followed by 5 g of 10% Pd/C. Hydrogenate at normal pressure and ambient temperature until the theoretical amount of hydrogen has been absorbed. Remove the catalyst by filtration, then isolate the tert-butyl (3S,5S)-5-methyl-3-propyl-2-oxo-4-morpholinecarboxylate by concentrating to dryness.

Step C: Ethyl (2S)-2-{(tert-butoxycarbonyl)[(1S)-2-hydroxy-1-methylethyl]amino}-pentanoate Introduce into a reactor 200 g of the compound obtained in the above Step, 500 ml of acetonitrile, 500 ml of water and 500 ml of hexane, and then add 33 g of lithium hydroxide hydrate and stir for 3 hours at 0° C.

The reaction mixture is then concentrated to dryness and the lithium salt obtained is dissolved in 1.5 liters of dimethylformamide and subsequently treated with 122 g of iodoethane at ambient temperature.

After removal of the dimethylformamide by evaporation, the residue obtained by concentrating to dryness is taken up in ethanol and filtered over silica to give ethyl (2S)-2-{(tert-butoxycarbonyl)[(1S)-2-hydroxy-1-methylethyl]amino}pentanoate in a yield of 60%.

Step D: N-[(S)-Ethoxycarbonyl-1-butyl]-N-(tert-butoxycarbonyl)-(S)-alanine

Introduce into a reactor 500 ml of dichloromethane, 500 ml of water and 500 ml of acetonitrile, and then add 141 g of sodium periodate and 1.35 g of hydrated ruthenium trichloride. Stir for 1 hour and add, rapidly, 200 g of the compound obtained in the above Step. At the end of the reaction, filter over Celite®, wash the organic phase and evaporate it to dryness to yield N-[(S)-ethoxycarbonyl-1-butyl]-N-(tert-butoxycarbonyl)-(S)-alanine.

Step E: N-[(S)-Ethoxycarbonyl-1-butyl]-(S)-alanine hydrochloride:

Introduce into a reactor 200 g of the compound obtained in the above Step and 1.5 liters of ethyl acetate, then bring the reaction mixture to 0° C. and pass a stream of HCl gas through it for 30 minutes. After stirring overnight at ambient temperature, the precipitate formed is filtered off, rinsed and dried to give N-[(S)-ethoxycarbonyl-1-butyl]-(S)-alanine hydrochloride in quantitative yield.

The invention claimed is:
1. A process for the synthesis of compounds of formula (I)

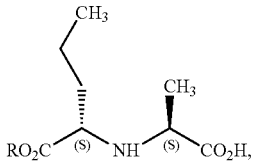

(I)

wherein R represents a linear or branched ($C_1$-$C_6$)alkyl group,
wherein a morpholinone of formula (III):

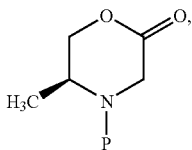

(III)

wherein P represents a protecting group for the amino function, is reacted
either with allyl bromide or allyl triflate, in the presence of a base, to yield a compound of formula (IV) having the (3S,5S) configuration:

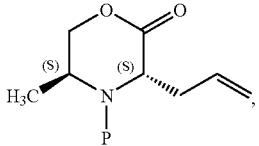

(IV)

which is hydrogenated in the presence of palladium-on-carbon,
or with iodopropane,
to yield a compound of formula (V):

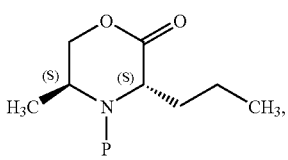

(V)

which is subjected to the action of LiOH, then to the action of an esterification reagent, to yield a compound of formula (VI):

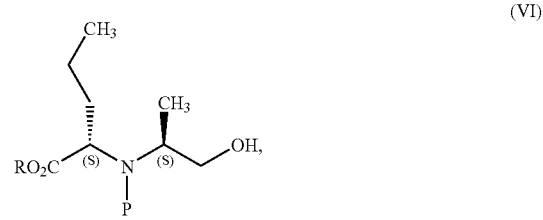

(VI)

which is reacted with an oxidizing agent to yield, after deprotection of the amino function, the compound of formula (I).

2. A process of claim 1, wherein R represents an ethyl group.

3. A process of claim 1, wherein P represents a tert-butoxycarbonyl group.

4. A process of claim 1, wherein the base used for the reaction between the compound of formula (III) and allyl bromide or allyl triflate is lithium diisopropylamide, sodium bis(trimethylsilyl)amide or potassium tert-butanolate.

5. A process of claim 1, wherein the esterification reagent is iodoethane.

6. A process of claim 1, wherein the oxidizing agent is $NaIO_4$ in the presence of $RuCl_3$.

7. A compound of formula (V):

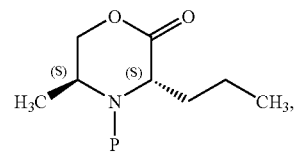

(V)

wherein P represents a tert-butoxycarbonyl group.

8. A compound of formula (VI):

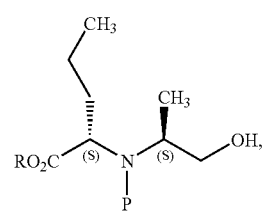

(VI)

wherein P represents a tert-butoxycarbonyl group and R represents an ethyl group.

* * * * *